United States Patent
Chen et al.

(10) Patent No.: US 10,633,376 B2
(45) Date of Patent: Apr. 28, 2020

(54) CRYSTALLINE FORMS OF JAK1-SELECTIVE INHIBITOR, PROCESSES FOR PREPARATION AND USE THEREOF

(71) Applicant: Crystal Pharmaceutical (Suzhou) Co., Ltd., Suzhou, Jiangsu (CN)

(72) Inventors: Minhua Chen, Suzhou (CN); Yanfeng Zhang, Suzhou (CN); Cunbo Yang, Suzhou (CN); Kai Liu, Suzhou (CN); Xiaoyu Zhang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/322,610

(22) PCT Filed: Aug. 3, 2017

(86) PCT No.: PCT/CN2017/095867
§ 371 (c)(1),
(2) Date: Feb. 1, 2019

(87) PCT Pub. No.: WO2018/024236
PCT Pub. Date: Feb. 8, 2018

(65) Prior Publication Data
US 2019/0177314 A1    Jun. 13, 2019

(30) Foreign Application Priority Data

Aug. 3, 2016    (CN) .......................... 2016 1 0628114

(51) Int. Cl.
| | | |
|---|---|---|
| *C07D 471/04* | (2006.01) | |
| *C07D 417/10* | (2006.01) | |
| *A61P 19/02* | (2006.01) | |
| *A61P 29/00* | (2006.01) | |
| *A61K 31/541* | (2006.01) | |

(52) U.S. Cl.
CPC .......... *C07D 417/10* (2013.01); *A61K 31/541* (2013.01); *A61P 19/02* (2018.01); *A61P 29/00* (2018.01); *C07D 471/04* (2013.01); *C07B 2200/13* (2013.01)

(58) Field of Classification Search
CPC ................................................... C07D 471/04
See application file for complete search history.

(56) References Cited

FOREIGN PATENT DOCUMENTS

| | | |
|---|---|---|
| CN | 104987333 A | 10/2015 |
| CN | 105061420 A | 11/2015 |
| CN | 105111206 A | 12/2015 |
| CN | 105111207 A | 12/2015 |
| CN | 105198876 A | 12/2015 |
| CN | 105198877 A | 12/2015 |
| CN | 105198878 A | 12/2015 |
| CN | 105198879 A | 12/2015 |
| CN | 105198880 A | 12/2015 |
| CN | 105218539 A | 1/2016 |
| WO | 2015117981 A1 | 8/2015 |
| WO | 2017012773 A1 | 1/2017 |
| WO | 2017133423 A1 | 8/2017 |

OTHER PUBLICATIONS

International Search Report for Application No. PCT/CN2017/095867, dated Oct. 27, 2017, 6 pages.

*Primary Examiner* — Bruck Kifle
(74) *Attorney, Agent, or Firm* — McCarter & English, LLP; Steven G. Davis; Wei Song

(57) ABSTRACT

The present disclosure relates to crystalline forms of JAK1-selective inhibitor, process for preparation and use for prevention and/or treatment of diseases associated with JAK family. The crystalline forms of the present disclosure show favorable properties such as simple preparation process, good stability, low hygroscopicity and good mechanical stability.

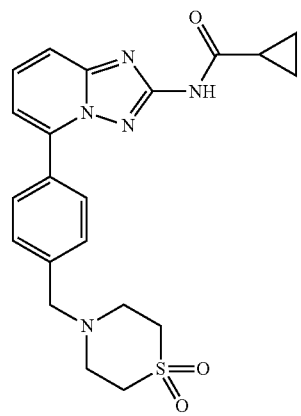

21 Claims, 11 Drawing Sheets

CRYSTALLINE FORMS OF JAK1-SELECTIVE INHIBITOR, PROCESSES FOR PREPARATION AND USE THEREOF

CROSS-REFERENCE TO RELATED APPLICATIONS

The present application is a U.S. national stage application, filed under 35 U.S.C. § 371(c), of International Application No. PCT/CN2017/095867, filed on Aug. 3, 2017, which claims the priority of Chinese Application No. 201610628114.X, filed on Aug. 3, 2016. The entire contents of the aforementioned applications are incorporated herein by reference.

TECHNICAL FIELD

The present disclosure relates to the field of pharmaceutical crystal technology. In particular, it relates to novel crystalline forms of Filgotinib, processes for preparation and use thereof.

BACKGROUND

Rheumatoid arthritis is an autoimmune disease that can cause chronic inflammation in joints and other parts of the body and leads to permanent joint damage and deformities. If not treated, rheumatoid arthritis can lead to substantial disability and pain due to the damage of joint function, which ultimately leads to shorter life expectancy. At present, the treatment of rheumatoid arthritis is far from satisfactory, and there is still a need to find new drugs that can be used for its treatment. Rheumatoid arthritis is a chronic disease that requires long-term therapy and repeated ingestion of the drugs. While long-term treatment may be a heavy burden on patients as well as doctors as the patient may be intolerant of the drug or become intolerant of the drug. In addition, higher dosage or frequency may lead to side effects of discomfort and/or lower patient compliance. The high incidence of rheumatoid arthritis (about 0.8% of adult worldwide) indicates its great social impact. The goal of rheumatoid arthritis therapy is not just to slow the progress of the disease, but also to relieve the pain in order to prevent joint damage and improve the quality of human life.

Crohn's disease is a type of inflammatory bowel disease that causes inflammation of the digestive tract, abdominal pain, severe diarrhea, intestinal obstruction, ulcers, fistula, anus cracks and other conditions, and is recurrent. In addition, people with Crohn's disease are at risk of malnutrition because their intestine cannot absorb the nutrients their bodies need from their diets. Inflammation caused by Crohn's disease may involve different areas of the human digestive tract, usually deep into the layers of intestine tissue, causing both pain and weakness, and even life-threatening complications. The recurrence rate of this disease is related to the extent of lesions, the enhancement of disease invasion, the prolongation of the disease course, the increase of age and other factors, and the mortality rate is also increased. Therefore, there is a need to develop therapeutic drugs that have a beneficial effect on this disease.

"JAK" refers to the Janus kinase (JAKs) family, a cytoplasmic tyrosine kinase that transduces cytokine signals from membrane receptors to STAT transcription factors, and is widely involved in many important biological processes such as inflammation, autoimmunity and immune regulation. The Janus kinase family comprises the following four JAK family members: JAK1, JAK2, JAK3 and TYK2. Among them, inhibition of JAK1 is essential for the anti-inflammatory treatment, while inhibition of JAK2, JAK3 and TYK2 is not necessary for anti-inflammatory treatment, and their inhibition process may cause some adverse reactions. For example, inhibition of JAK2 may causes anemia and inhibition of JAK3 may inhibit immune function. JAK1 is a target for immune-inflammatory diseases, and its inhibitors are beneficial for the treatment of immune inflammatory disorder diseases such as rheumatoid arthritis and Crohn's disease.

Filgotinib (GLPG0634) is a JAK1 selective inhibitor with IC50 of 10 nM, 28 nM, 810 nM, and 116 nM for JAK1, JAK2, JAK3, and TYK2, respectively. Among them, $IC_{50}$ (half maximal inhibitory concentration) refers to the measured semi-inhibitory concentration, which can indicate the half amount of a drug or substance (inhibitor) in inhibiting certain biological procedures. The lower the value, the stronger the inhibition ability of the drug is. Therefore, Filgotinib shows a high degree of selectivity in inhibiting JAK1. Clinical trials by Gilead have shown that Filgotinib does not cause an anemia and abnormal increase in low density lipoprotein (LDL), and the free form is registered for clinical use. The results show that Filgotinib has a very good application prospect in the treatment of rheumatoid arthritis and Crohn's disease.

The chemical name of Filgotinib is: N-[5-[4-[(1,1-dioxo-1-thiomorpholin-4-yl)methyl]phenyl][1,2,4]triazolo [1,5-a]pyridin-2-yl]cyclopropanecarboxamide. The chemical formula is $C_{21}H_{23}N_5O_3S$. The molecular weight is 425.5. The chemical structure is shown as below:

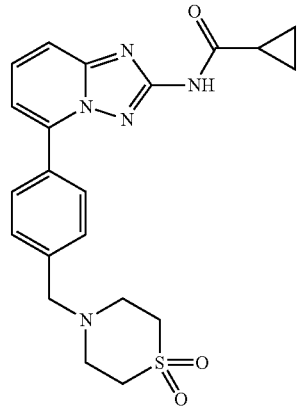 [SMILES: O=C(Nc1nc2cccc(-c3ccc(CN4CCS(=O)(=O)CC4)cc3)n2n1)C1CC1]

WO2010149769A1 (which is incorporated herein by reference) disclosed the confirmation, preparation and use of the free form of Filgotinib, however, the patent does not disclose information of the final solid form of Filgotinib free form. CN105111206A proved that the solid in WO2010149769A1 is amorphous. The analysis of prior art of the free form are as follows:

| Patent | Crystalline form | Disadvantages |
| --- | --- | --- |
| CN105960407A | Pattern 1, 3 and 4 of free form | Preparation methods of the three crystalline forms are all complicated. Heating cooling cycle between ambient temperature and 50° C. is required. XRPD pattern indicates that the crystallinity of pattern 3 is poor. |

| Patent | Crystalline form | Disadvantages |
|---|---|---|
| CN105061420A | Form H1, H2, H3, H4 of free form | The preparation methods are complicated, and all of the preparation methods need the procedure of heating to a high temperature of 70-90° C. and then cooling to 0-30° C. |
| CN105198880A | Form A of free form | The yield is low, ranging from 76% to 88%. XRPD pattern indicates that the crystallinity is poor. |
| CN105218539A | Form B of free form | Stability is poor. Sample was tested by XRPD after being placed at 92.5% humidity for 5 days and 10 days and the results show that the stability is poor. The solubility is low. The solubility in water is 41.28 µg/mL. The yield is low, and is in the range of 70-86%. |
| CN105198879A | Form C of free form | Stability is poor. Sample was tested by XRPD after being placed at 92.5% humidity for 5 days and 10 days and the results show that the stability is poor. The solubility is low. The solubility in water is 42.22 µg/mL. The yield is low and is in the range of 79-86%. |
| CN105111207A | Form D of free form | Stability is poor. XRPD is tested after being placed at 92.5% humidity for 5 days and 10 days and the results show that the stability is poor. The solubility is low. The solubility in water is 55.26 µg/mL. The yield is low and is in the range of 66-69%. |
| CN105111206A | Form E of free form | Stability is poor. XRPD is tested after being placed at 92.5% humidity for 5 days and 10 days and the results show that the stability is poor. The yield is low and is in the range of 66-71%. The solvents, N,N-dimethylformamide and DMSO, used in the preparation method have high boiling points of 153° C. and 189° C., respectively, which makes it difficult to remove the solvents from the final products and easily cause solvent residue. |
| CN105198878A | Form F of free form | The solubility is low. The solubility in water is 50.98 µg/mL. The yield is low and is in the range of 53-56%. |
| CN105198877A | Form G of free form | The yield is low and is in the range of 55-76%. DMSO used in the preparation method has high boiling point of 189° C., which makes it difficult to remove the solvents from the final products and easily cause solvent residue. |
| CN105198876A | Form H of free form | The yield is low and is 56%. The solubility is low. The solubility in water is 12.77 µg/mL. |

In summary, crystalline forms of the prior art have disadvantages of complicated preparation methods, poor crystallinity, low solubility, low yield, poor stability, difficulty in drying, and ease to cause solvent residue. The inventors of present disclosure found through experiments and comprehensive analysis that Pattern 4 in CN105960407A has better properties than other crystalline forms of the prior art, such as better stability, not easy to change to other crystalline forms at room temperature, better crystallinity, easier to dry, and not easy to cause solvent residues. However, the inventors have found through experiments that Pattern 4 also has the following disadvantages such as the low solubility, high hygroscopicity, poor mechanical stability under certain mechanical force, and complicated preparation method which needs a thermal cycle between the environment temperature and 50° C. It is not conducive to the scale up of the downstream process. Therefore, it is necessary to carry out polymorph screening, so that the developed novel crystalline form can overcome the disadvantages of the prior art and is more suitable for industrial production.

The invention overcomes the disadvantages of the prior art, and the novel crystalline forms have the advantages such as simple preparation method, high solubility, good crystallinity, high purity, low hygroscopicity, good stability, especially good mechanical stability compared with the Pattern 4 of CN105960407A. These advantages make the novel crystalline form suitable for the industrial production of formulation and future drug application, which is of great economic value.

SUMMARY

The main objective of the present disclosure is to provide novel crystalline forms of Filgotinib, processes for preparation and use thereof.

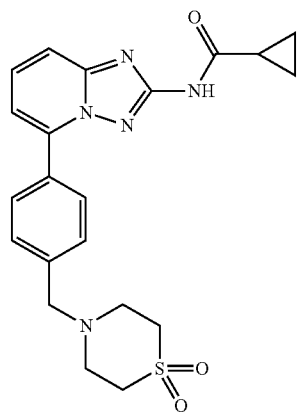 [SMILES: O=C(Nc1nc2cccc(-c3ccc(CN4CCS(=O)(=O)CC4)cc3)n2n1)C1CC1]

Without any limitation being implied, in a specific example of the present disclosure, the X-ray powder diffraction pattern of crystalline form CS1 is substantially as depicted in FIG. 1.

According to the objective of the present disclosure, crystalline form CS1 of Filgotinib is provided (hereinafter referred to as Form CS1). Form CS1 of the present disclosure is an anhydrate.

The X-ray powder diffraction pattern of Form CS1 of the present disclosure shows characteristic peaks at 2theta values of 10.3°±0.2°, 13.7°±0.2° and 16.1°±0.2° using CuKα radiation.

Furthermore, the X-ray powder diffraction pattern of Form CS1 shows 1 or 2 or 3 characteristic peaks at 2theta values of 18.0°±0.20, 21.7°±0.2° and 24.7°±0.2°.

Furthermore, the X-ray powder diffraction pattern of Form CS1 shows 1 or 2 characteristic peaks at 2theta values of 8.6°±0.2° and 19.4°±0.2°.

In a preferable example, the X-ray powder diffraction pattern of Form CS1 shows characteristic peaks at 2theta values of 10.3°±0.2°, 13.7°±0.2°, 16.1°±0.2°, 18.0°±0.2°, 21.7°±0.2°, 24.7°±0.2°, 8.6°±0.2° and 19.4°±0.2°.

According to the objective of the present disclosure, a process for preparing Form CS1 is also provided. The process comprises suspending Filgotinib hydrochloride into halogenated aromatic hydrocarbons with adding base, stirring for crystallization at certain temperature, and then isolating the solid to obtain a halogenated aromatic hydrocarbon solvate. Form CS1 of the present disclosure is obtained via a desolvation process by heating the halogenated aromatic hydrocarbon solvate under nitrogen protection.

Furthermore:

Said halogenated aromatic hydrocarbon is a solvent or a mixture of solvents selected from aromatic hydrocarbons with substituted aromatic rings;

Preferably, said halogenated aromatic hydrocarbon is a solvent or a mixture of solvents selected from chlorobenzene and bromobenzene;

More preferably, said halogenated aromatic hydrocarbon is chlorobenzene;

Said base is inorganic base;

Preferably, said base is a base or a mixture of bases selected from sodium hydroxide, potassium hydroxide and calcium hydroxide;

More preferably, said base is sodium hydroxide;

Said crystallization temperature is 25-0° C.;

Preferably, said crystallization temperature is 10-0° C.;

More preferably, said crystallization temperature is 5° C.;

Said desolvation temperature is 150-195° C.;

Preferably, said desolvation temperature is 190° C.;

According to the objective of the present disclosure, crystalline form CS2 of Filgotinib is provided (hereinafter referred to as Form CS2). Form CS2 of the present disclosure is an anhydrate.

The X-ray powder diffraction pattern of Form CS2 of the present disclosure shows characteristic peaks at 2theta values of 17.5°±0.2°, 18.1°±0.2° and 8.0°±0.2° using CuKα radiation.

Furthermore, the X-ray powder diffraction pattern of Form CS2 shows 1 or 2 or 3 characteristic peaks at 2theta values of 24.7°±0.2°, 17.2°±0.2° and 27.4°±0.2°.

Furthermore, the X-ray powder diffraction pattern of Form CS2 shows 1 or 2 or 3 characteristic peaks at 2theta values of 7.2°±0.2°, 11.0°±0.2° and 19.0°±0.2°.

In a preferable example, the X-ray powder diffraction pattern of Form CS2 shows characteristic peaks at 2theta values of 17.5°±0.2°, 18.1°±0.2°, 8.0°±0.2°, 24.7°±0.2°, 17.2°±0.2°, 27.4°±0.2°, 7.2°±0.2°, 11.0°±0.2° and 19.0°±0.2°.

Without any limitation being implied, the X-ray powder diffraction pattern of Form CS2 in a specific example of the present disclosure is substantially as depicted in FIG. 4.

According to the objective of the present disclosure, a process for preparing Form CS2 is also provided. The process comprises suspending Filgotinib hydrochloride into carboxylic acid with adding base, stirring for crystallization at certain temperature, isolating the solid to obtain a carboxylic acid solvate. Form CS2 of the present disclosure is obtained via a desolvation process by heating the carboxylic acid solvate under nitrogen protection.

Furthermore:

Said carboxylic acid is a carboxylic acid or a mixture of carboxylic acids selected from C1-C3 carboxylic acids;

Preferably, said carboxylic acid is acetic acid;

Said base is inorganic base;

Preferably, said base is a base or a mixture base selected from sodium hydroxide, potassium hydroxide and calcium hydroxide;

More preferably, said base is sodium hydroxide;

Said crystallization temperature is 25-0° C.;

Preferably, said crystallization temperature is 10-0° C.;

More preferably, said crystallization temperature is 5° C.;

Said desolvation temperature is 150-195° C.;

Preferably, said desolvation temperature is 190° C.;

According to the objective of the present disclosure, crystalline form CS3 of Filgotinib is provided (hereinafter referred to as Form CS3). Form CS3 of the present disclosure is a complex of Filgotinib and acetic acid (hereinafter referred to as acetic acid complex), including but not limited to solvate or salt.

The X-ray powder diffraction pattern of Form CS3 of the present disclosure shows characteristic peaks at 2theta values of 11.8°±0.2°, 14.1°±0.2° and 17.8°±0.2° using CuKα radiation.

Furthermore, the X-ray powder diffraction pattern of Form CS3 shows 1 or 2 or 3 characteristic peaks at 2theta values of 18.4°±0.2°, 20.5°±0.2° and 22.9°±0.2°.

Furthermore, the X-ray powder diffraction pattern of Form CS3 shows 1 or 2 or 3 characteristic peaks at 2theta values of 25.7°±0.2°, 11.5°±0.2° and 23.6°±0.2°.

In a preferable example, the X-ray powder diffraction pattern of Form CS3 shows characteristic peaks at 2theta values of 11.8°±0.2°, 14.1°±0.2°, 17.8°±0.2°, 18.4°±0.2°, 20.5°±0.2°, 22.9°±0.2°, 25.7°±0.2°, 11.5°±0.2° and 23.6°±0.2°.

Without any limitation being implied, in a specific example of the present disclosure, the X-ray powder diffraction pattern of Form CS3 in a specific example of the present disclosure is substantially as depicted in FIG. 12.

According to the objective of the present disclosure, a process for preparing Form CS3 is also provided. The process comprises suspending Filgotinib hydrochloride into acetic acid, adding base to the suspension, stirring for crystallization at certain temperature and isolating to obtain Form CS3.

Furthermore:

Said base is inorganic base;

Preferably, said base is a base or a mixture of bases selected from sodium hydroxide, potassium hydroxide and calcium hydroxide;

More preferably, said base is sodium hydroxide;

Said crystallization temperature is 25-0° C.;

Preferably, said crystallization temperature is 10-0° C.;

More preferably, said crystallization temperature is 5° C.

Form CS1, Form CS2 and Form CS3 of the present disclosure have the following advantages:

1) The crystalline forms of the present disclosure have good crystallinity.

2) The crystalline forms of the present disclosure have good stability. The crystalline form of Form CS1 doesn't change when placed under the conditions of 25° C./60% RH and 40° C./75% RH for 3 weeks. The crystalline form of Form CS2 doesn't change when placed under the conditions of 25° C./60% RH, 40° C./75% RH and 60° C./75% RH for 3 weeks.

3) The crystalline forms of the present disclosure have low hygroscopicity. The weight gain of Form CS2 at 80% RH is 0.198%. Form CS2 is almost no hygroscopic.

4) The crystalline forms of the present disclosure have good mechanical stability. The crystalline forms of Form CS2 and CS3 don't change after grinding.

5) The crystalline forms of the present disclosure have high yields. The yields of CS1 and CS2 are 100%.

6) The process for preparing the crystalline forms of the present disclosure doesn't use high boiling point solvents. The crystals are easily dried and not easy to cause solvent residue.

7) The crystalline forms of the present disclosure have high solubility. Particularly in SGF (simulated gastric fluids, pH=1.8), FaSSIF (fasted state simulated intestinal fluids, pH=6.5), FeSSIF (fed state simulated intestinal fluids, pH=5.0) and pure water, the solubility of Form CS1 and CS2 is higher than that of Pattern 4 of CN105960407A.

Said "room temperature" refers to 10-30° C.

Said "stirring" is accomplished by using a conventional method in the field such as a magnetic stirring or a mechanical stirring and the stirring speed is 50 to 1800 r/min, preferably the magnetic stirring speed is 300 to 900 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or a higher temperature. The drying temperature is from room temperature to about 60° C., or to 40° C., or to 50° C. The drying time can be 2 to 48 hours, or overnight. Drying is accomplished in a fume hood, oven or vacuum oven.

Said "desolvation" includes, but is not limited to, heating with DSC, vacuum drying, etc., and includes other methods. The DSC heating rate comprises, but is not limited to 20° C./min.

In the present disclosure, "crystal" or "crystalline form" refers to the crystal or the crystalline form being identified by the X-ray diffraction pattern shown herein. Those skilled in the art are able to understand that physicochemical properties discussed herein can be characterized; the experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In addition, the experimental error of the diffraction peak angle is usually 5% or less, and the error of these angles should also be taken into account, and an error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

"Crystalline form" and "polymorphic form" as well as other related terms in the present disclosure refer to the solid compounds whose crystal structure is being in a special crystal form state. The difference in the physical and chemical properties of the polymorphs may be embodied in storage stability, compressibility, density, dissolution rate, etc. In extreme cases, the difference in solubility or dissolution rate may result in inefficient drugs, even developing toxicity.

In some examples, Form CS1, Form CS2 and Form CS3 of the present disclosure are pure, single forms and substantially free of any other crystalline forms. In the present disclosure, when "substantially free of" is used for describing a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the range of number should not be narrowly understood as a value or numerical value range. It should be understood by those skilled in the art that the specific numerical value can be floated according to the specific technical environment on the basis that the spirit and principle of the present disclosure are not depart from the spirit and principle of the present disclosure. In the present disclosure, the number of floating ranges which can be expected by one of skilled in the art is represented by the term "about".

According to the objective of the present disclosure, a pharmaceutical composition is provided, said pharmaceutical composition comprises a therapeutically and/or prevention effective amount of Form CS1, Form CS2, Form CS3 or combinations thereof and pharmaceutically acceptable carriers, diluents or excipients.

Furthermore, Form CS1, Form CS2 or Form CS3 or combinations thereof can be used for preparing drugs inhibiting JAK, particularly used for preparing drugs inhibiting JAK1.

Furthermore, Form CS1, Form CS2 or Form CS3 or combinations thereof can be used for preparing drugs treating rheumatoid arthritis and Crohn's disease.

The crystalline form of Form CS1 of the present disclosure doesn't change for at least 3 weeks when placed under the condition of 25° C./60% RH and 40° C./75% RH. The crystalline form of Form CS2 doesn't change for at least 3 weeks when placed under the condition of 25° C./60% RH, 40° C./75% RH and 60° C./75% RH. Form CS1 and Form CS2 of the present disclosure have good stability. The weight gain of Form CS2 at 80% RH is 0.198%. Form CS2 is almost non-hygroscopic. Form CS2 and Form CS3 of the present disclosure have good mechanical stabilities without crystal transformation observed during grinding. Form CS1 and Form CS2 of the present disclosure have relatively high solubility in saturated solutions prepared with SGF (simulated gastric fluids), FeSSIF (fed state simulated intestinal fluids, pH5.0), FaSSIF (fasted state simulated intestinal fluids, pH6.5) and pure water.

DETAILED DESCRIPTION OF THE DISCLOSURE

The present disclosure is further illustrated by the following examples which describe the preparation and use of the crystalline forms of the disclosure in detail. It is obvious to those skilled in the art that many changes in the materials and methods can be accomplished without departing from the scope of the disclosure.

The instruments and methods used to collect data:

X-ray powder diffraction pattern in the present disclosure is acquired by a Panalytical Empyrean X-ray powder diffractometer. The parameters of the X-ray powder diffraction method of the present disclosure are as follows:
  X-ray Reflection: Cu, Kα
  Kα1 (Å): 1.540598. Kα2 (Å): 1.544426
  Kα2/Kα1 intensity ratio: 0.50
  Voltage: 45 (kV)
  Current: 40 (mA)
  Scan range: from 3.0 degree to 40.0 degree Differential scanning calorimetry (DSC) data in the present disclosure were acquired by a TA Q2000. The parameters of the DSC method of the present disclosure were as follows:
  Heating rate: 10° C./min
  Purge gas: nitrogen
  In particular, scanning rate of the used DSC in the embodiment part of the present disclosure is 20° C./min during heating.

Thermal gravimetric analysis (TGA) data in the present disclosure are acquired by a TA Q500. The parameters of the TGA method of the present disclosure were as follow:
  Heating rate: 10° C./min
  Purge gas: nitrogen Proton nuclear magnetic resonance spectrum data ($^1$H NMR) are collected from a Bruker Avance II DMX 400M HZ NMR spectrometer. 1-5 mg of sample was weighed, and dissolved in 0.5 mL of deuterated dimethyl sulfoxide or deuterated water to obtain a solution with a concentration of 2-10 mg/mL.

Dynamic Vapor Sorption (DVS) is measured via a SMS (Surface Measurement Systems Ltd.) intrinsic DVS instrument. Its control software is DVS-Intrinsic control software, and its analysis software is DVS-Intrinsic Analsis software. Typical Parameters for DVS test are as follows:
  Temperature: 25° C.
  Gas and flow rate: $N_2$, 200 mL/min
  dm/dt: 0.002%/min
  RH range: 0% RH to 95% RH Unless otherwise specified, the following examples were conducted at room temperature.

Free base or known crystalline form of Filgotinib.HCl.3H$_2$O used in the following examples can be prepared by known method in WO2010149769A1.

The reagents used are commercially available, and the purity is analytical grade purity.

Example 1 Preparation of Form CS1

Figure 13:
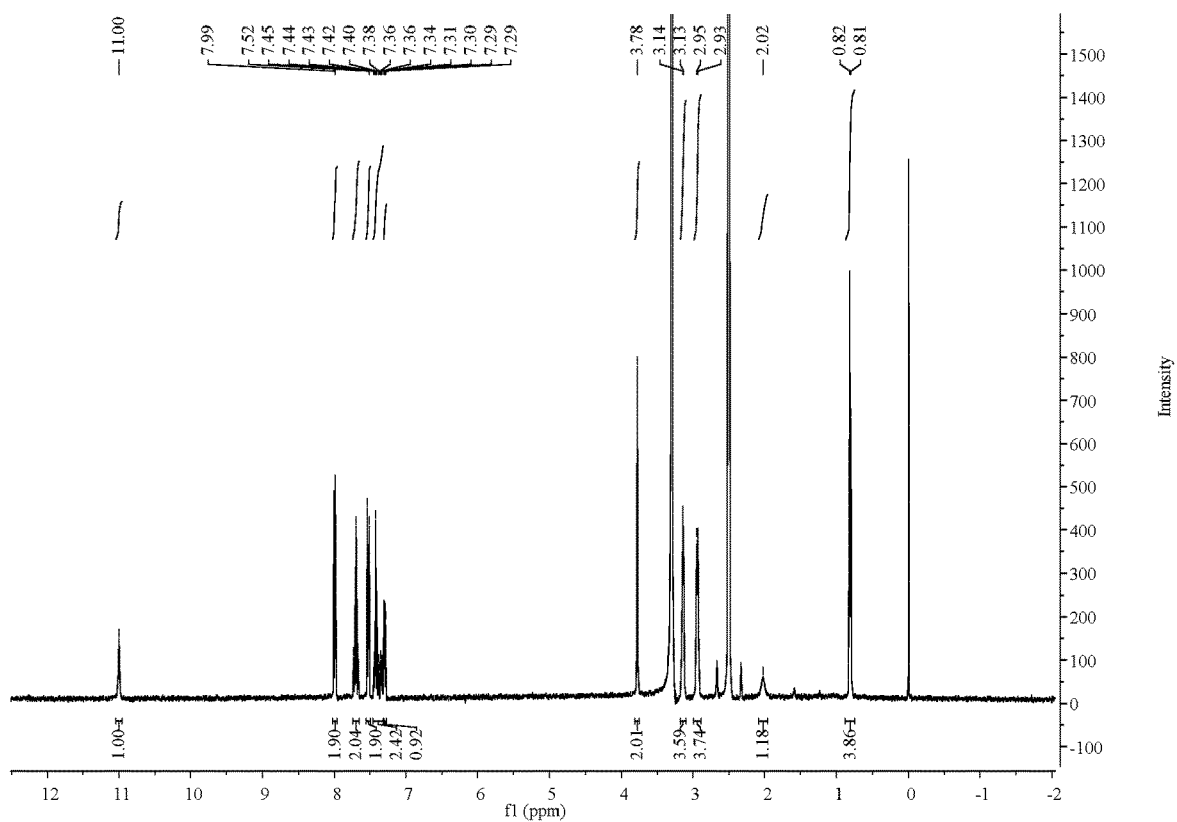
FIG. 13 shows a $^1$H NMR spectrum of chlorobenzene solvate.
Figure 14:
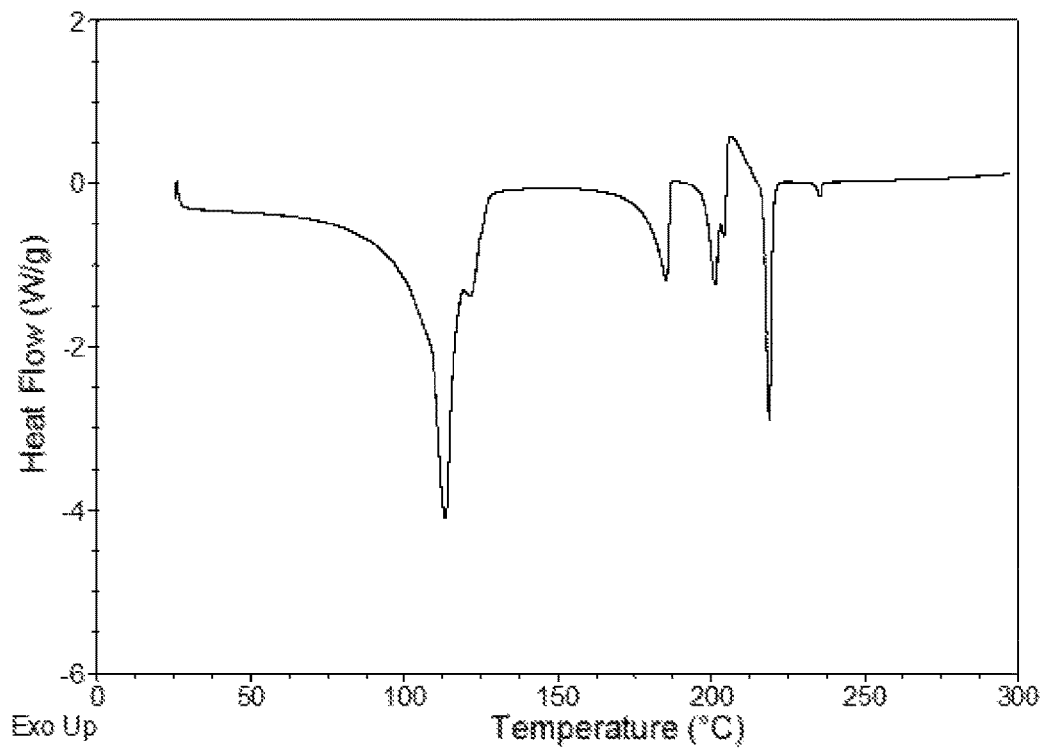
FIG. 14 shows a DSC curve of chlorobenzene solvate.
Figure 15:
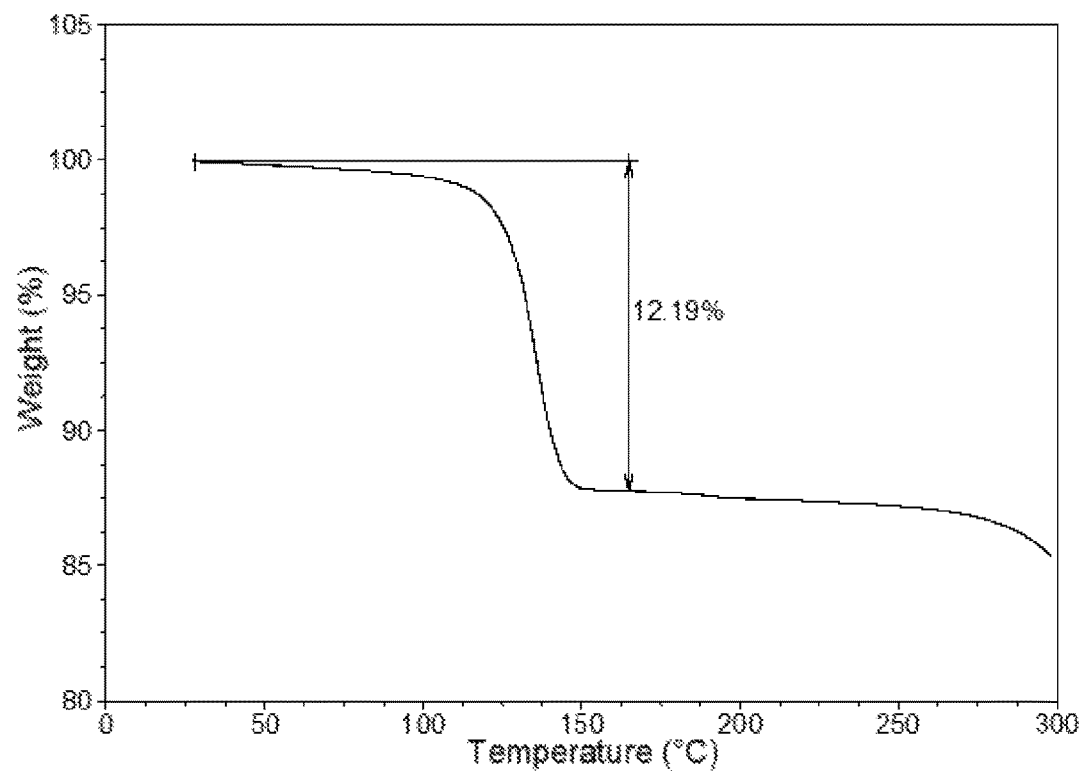
FIG. 15 shows a TGA curve of chlorobenzene solvate.
Figure 16:
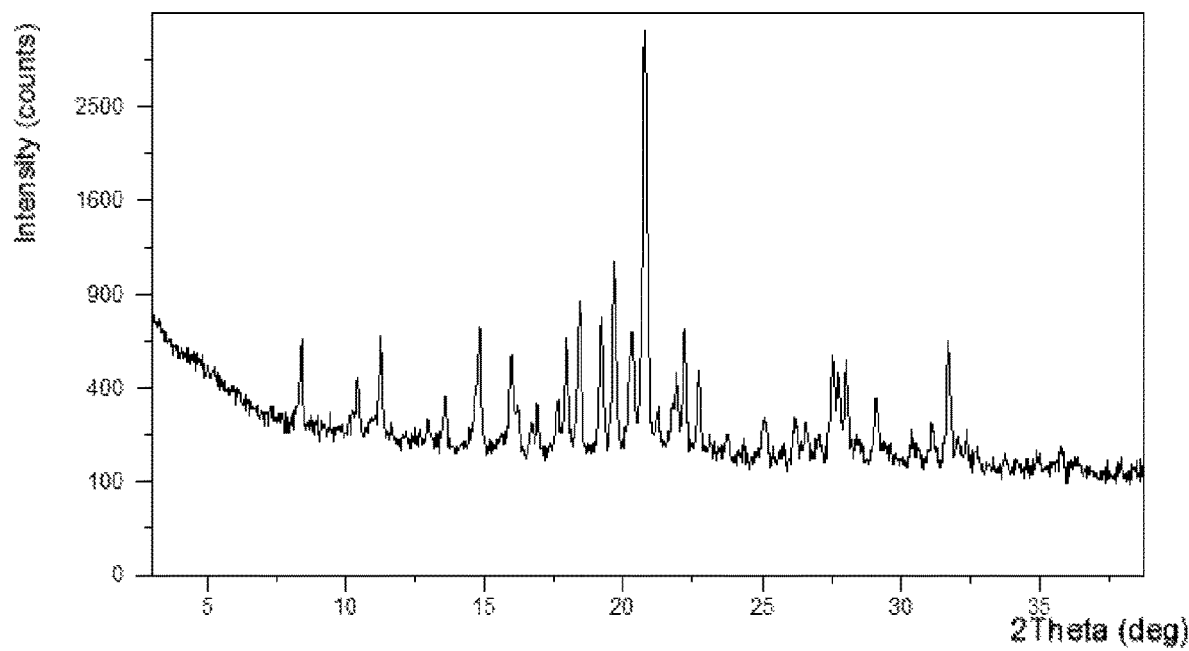
FIG. 16 shows an XRPD pattern of chlorobenzene solvate.

500.2 mg of Filgotinib hydrochloride was weighted into 5.0 mL of chlorobenzene. After stirring at room temperature for 10 min, 0.55 mL of sodium hydroxide aqueous solution (2 mol/L) was added dropwise, and the suspension was stirred at 5° C. for 32 hours for reaction. The suspension was filtered and washed with 3.0 mL of pure water, followed by vacuum drying at room temperature. White powder was obtained. The white powder was identified to be chlorobenzene solvate by $^1$H NMR (FIG. 13), DSC (FIG. 14), TGA (FIG. 15) and XRPD (FIG. 16), and the $^1$H NMR data of chlorobenzene solvate are: $^1$H NMR (400 MHz, DMSO) δ 11.00 (s, 1H), 8.00 (d, J=8.3 Hz, 2H), 7.74-7.65 (m, 2H), 7.53 (d, J=8.3 Hz, 2H), 7.46-7.32 (m, 2.5H), 7.30 (dd, J=6.7, 1.9 Hz, 1H), 3.78 (s, 2H), 3.14 (d, J=5.1 Hz, 4H), 2.94 (d, J=5.8 Hz, 4H), 0.81 (d, J=6.2 Hz, 4H).

17.56 mg of chlorobenzene solvate obtained above was heated to 190° C. using DSC (heating rate was 20° C./min), then white solid was obtained and the yield was 100%.

The obtained crystalline solid was identified to be Form CS1 of the present disclosure, and the XRPD data were listed in Table 1.

TABLE 1

| 2θ (±0.2°) | d spacing | Intensity % |
| --- | --- | --- |
| 4.85 | 18.22 | 1.43 |
| 7.23 | 12.23 | 11.53 |
| 7.98 | 11.07 | 4.24 |
| 8.55 | 10.34 | 93.17 |
| 10.34 | 8.56 | 40.74 |
| 10.98 | 8.06 | 11.21 |
| 11.63 | 7.61 | 5.97 |
| 11.89 | 7.44 | 11.10 |
| 12.35 | 7.17 | 1.19 |
| 13.09 | 6.76 | 41.40 |
| 13.66 | 6.48 | 9.47 |
| 14.52 | 6.10 | 2.84 |
| 14.93 | 5.93 | 1.48 |
| 15.59 | 5.68 | 7.04 |
| 15.88 | 5.58 | 17.13 |
| 16.13 | 5.50 | 37.58 |
| 16.36 | 5.42 | 37.55 |
| 17.30 | 5.12 | 25.53 |

TABLE 1-continued

| 2θ (±0.2°) | d spacing | Intensity % |
|---|---|---|
| 17.57 | 5.05 | 16.34 |
| 17.98 | 4.93 | 16.39 |
| 19.43 | 4.57 | 100.00 |
| 19.69 | 4.51 | 90.76 |
| 20.12 | 4.41 | 65.47 |
| 20.43 | 4.35 | 27.35 |
| 21.70 | 4.10 | 8.27 |
| 22.10 | 4.02 | 7.94 |
| 23.01 | 3.87 | 16.09 |
| 23.85 | 3.73 | 6.65 |
| 24.73 | 3.60 | 8.37 |
| 25.36 | 3.51 | 5.69 |
| 25.93 | 3.44 | 3.58 |
| 26.35 | 3.38 | 2.82 |
| 26.92 | 3.31 | 2.68 |
| 27.43 | 3.25 | 8.87 |
| 28.01 | 3.19 | 5.87 |
| 28.72 | 3.11 | 2.16 |
| 29.52 | 3.03 | 7.06 |
| 31.42 | 2.85 | 5.72 |
| 33.15 | 2.70 | 1.82 |
| 36.24 | 2.48 | 1.41 |

Figure 1:
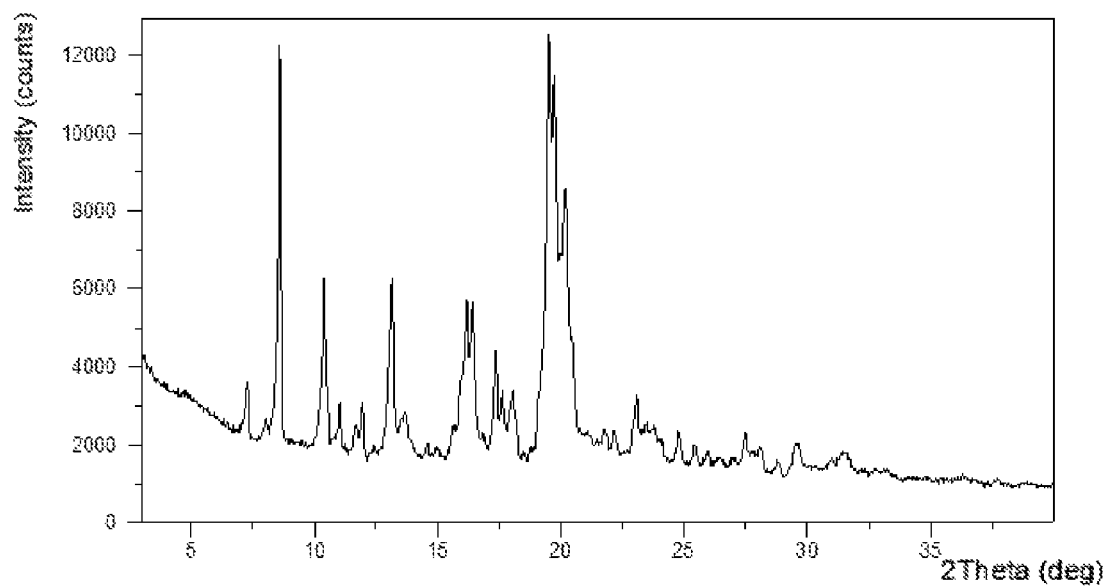
FIG. 1 shows an XRPD pattern of Form CS1.
Figure 2:
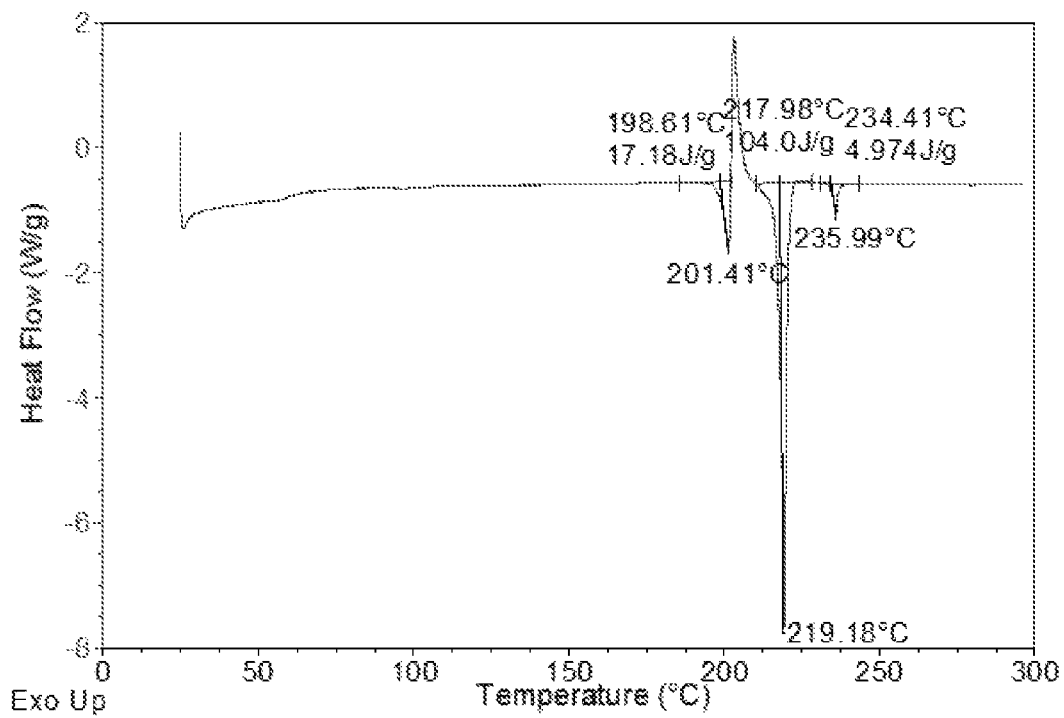
FIG. 2 shows a DSC curve of Form CS1.
Figure 3:
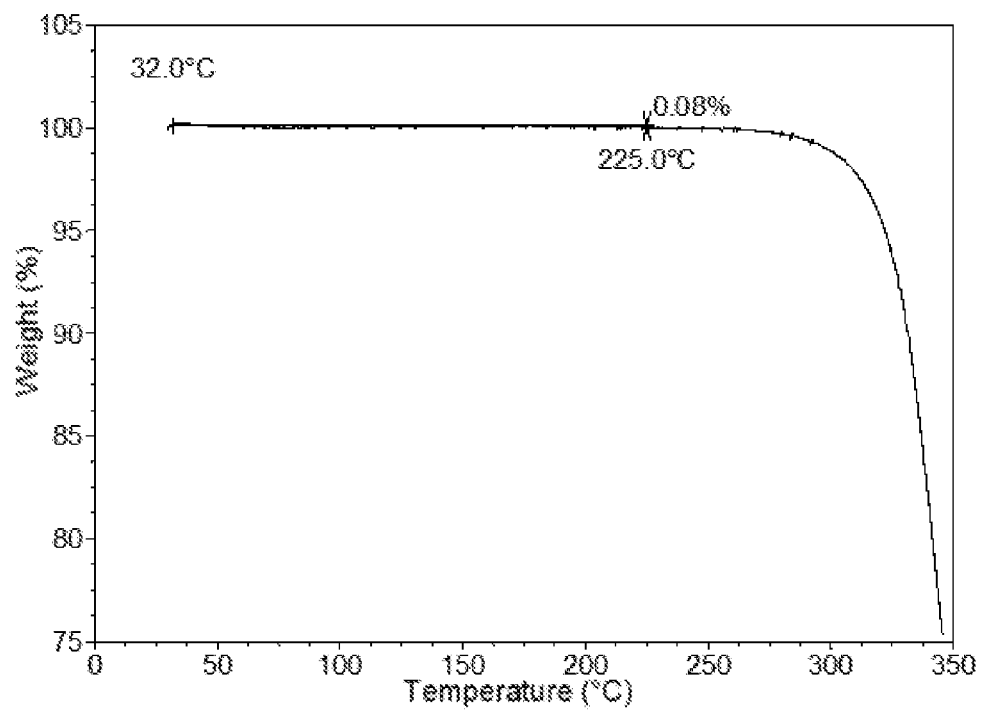
FIG. 3 shows a TGA curve of Form CS1.

The DSC curve of Form CS1 is substantially as depicted in FIG. 2. The first endothermic peak is at around 199° C., followed by an exothermic peak, and the second endothermic peak is at around 218° C. The TGA curve of Form CS1 shows about 0.1% weight loss when heated to 225° C., which is substantially as depicted in FIG. 3.

Example 2 Preparation of Form CS3

Figure 9:
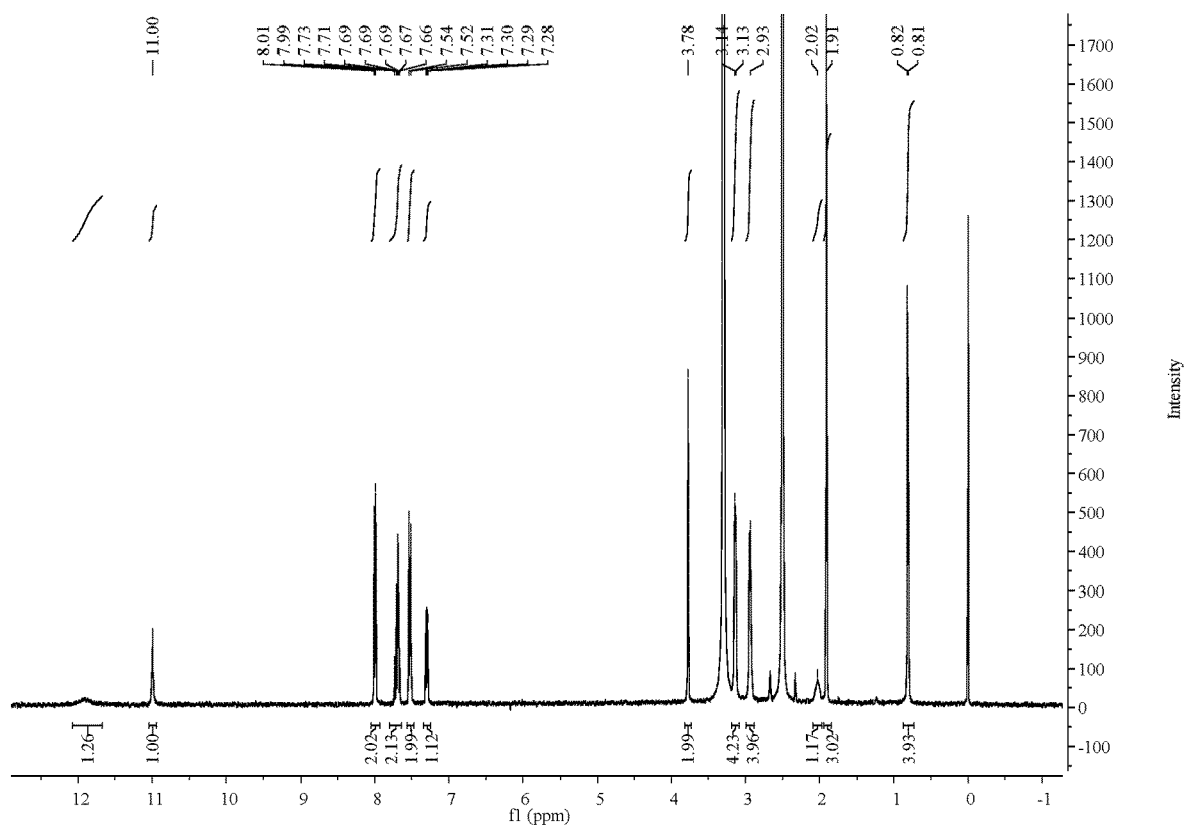
FIG. 9 shows a $^1$H NMR spectrum of Form CS3.
Figure 10:
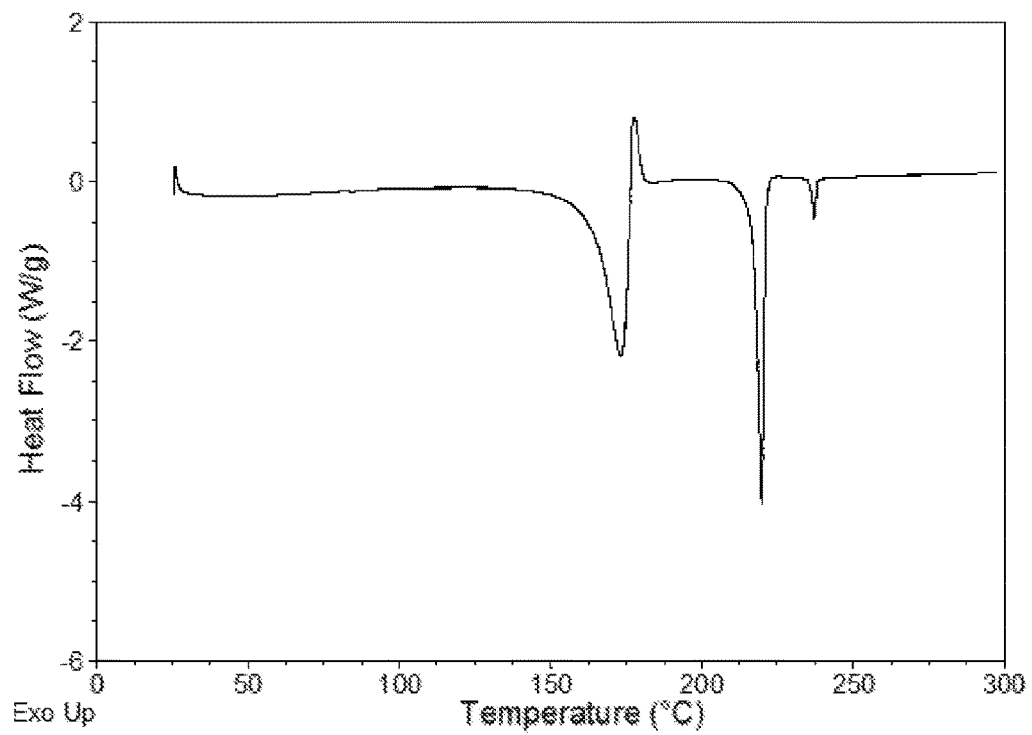
FIG. 10 shows a DSC curve of Form CS3.
Figure 11:
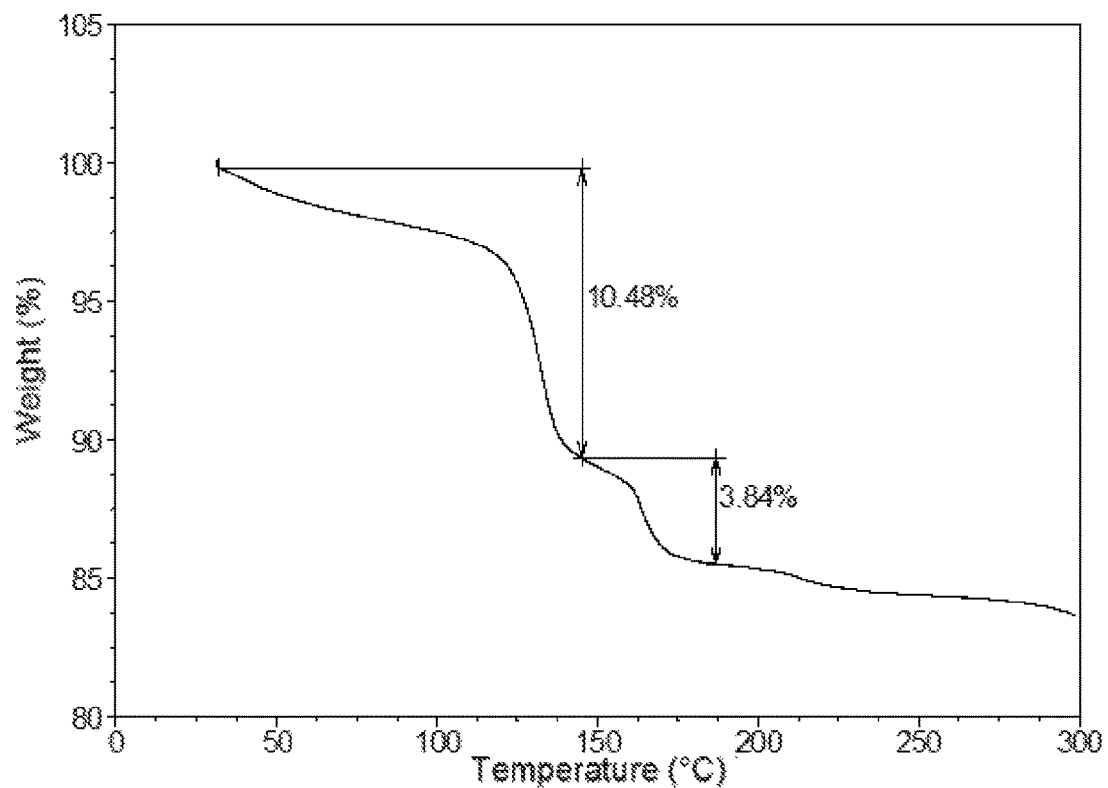
FIG. 11 shows a TGA curve of Form CS3.
Figure 12:
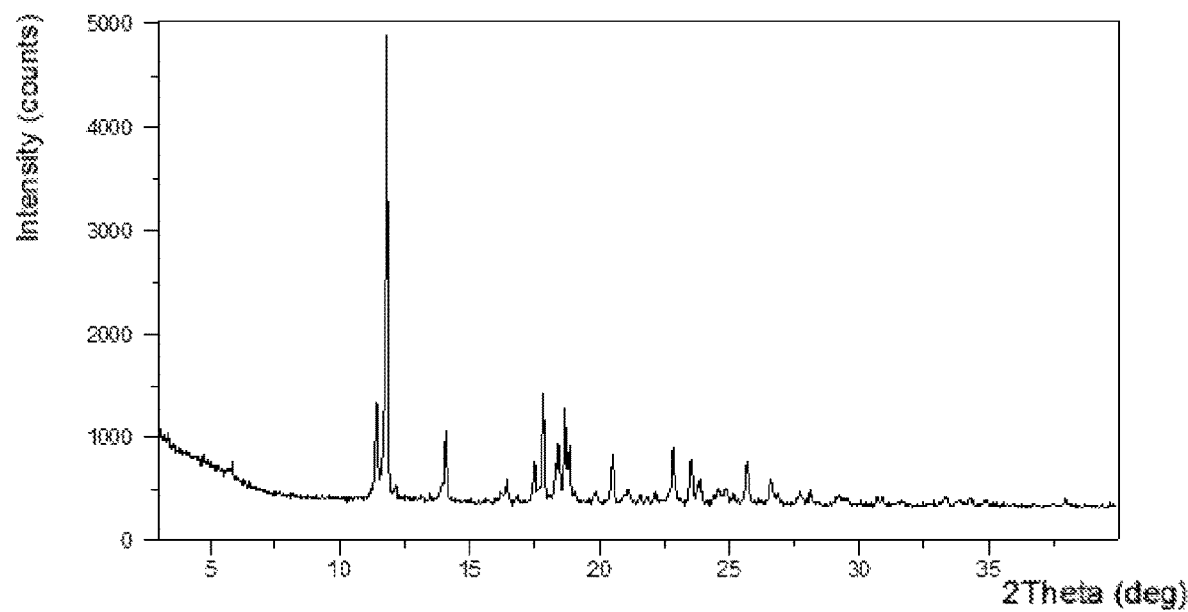
FIG. 12 shows an XRPD pattern of Form CS3.

499.7 mg of Filgotinib hydrochloride was added into 5.0 mL of acetic acid. After stirring at room temperature for 10 min, 5.55 mL of sodium hydroxide aqueous solution (2 mol/L) was added dropwise, and the suspension was stirred at 5° C. for 32 hours for reaction. The suspension was filtered and washed with 3.0 mL of pure water, followed by vacuum drying at room temperature. White powder was obtained. The product was weighed and the calculated yield is 84%. The obtained crystalline solid was identified to be Form CS3 of the present disclosure by $^1$H NMR (FIG. 9), DSC (FIG. 10) and TGA (FIG. 11). Form CS3 is acetic acid complex, and $^1$H NMR data of this acetic acid complex are: $^1$H NMR (400 MHz, DMSO) δ 12.07-11.67 (m, 1H), δ 11.00 (s, 1H), 8.00 (d, J=8.2 Hz, 2H), 7.80-7.64 (m, 2H), 7.53 (d, J=8.2 Hz, 2H), 7.30 (dd, J=6.7, 1.8 Hz, 1H), 3.78 (s, 2H), 3.14 (d, J=5.1 Hz, 4H), 2.93 (s, 4H), 2.02 (s, 1H), 1.91 (s, 3H), 0.81 (d, J=6.2 Hz, 4H). XRPD pattern of Form CS3 in this example was substantially as depicted in FIG. 12, and the XRPD data were listed in Table 2.

TABLE 2

| 2θ (±0.2°) | d spacing | Intensity % |
|---|---|---|
| 4.87 | 18.16 | 0.88 |
| 5.86 | 15.08 | 2.10 |
| 11.45 | 7.73 | 25.18 |
| 11.84 | 7.47 | 100.00 |
| 12.19 | 7.26 | 3.39 |
| 14.09 | 6.28 | 20.07 |
| 16.24 | 5.46 | 4.58 |
| 16.43 | 5.40 | 7.63 |
| 16.82 | 5.27 | 2.88 |
| 17.50 | 5.07 | 15.53 |
| 17.84 | 4.97 | 34.07 |
| 18.43 | 4.81 | 23.85 |
| 18.67 | 4.75 | 34.24 |
| 18.84 | 4.71 | 25.04 |

TABLE 2-continued

| 2θ (±0.2°) | d spacing | Intensity % |
|---|---|---|
| 19.07 | 4.66 | 5.39 |
| 19.91 | 4.46 | 5.50 |
| 20.51 | 4.33 | 17.94 |
| 21.11 | 4.21 | 6.14 |
| 21.58 | 4.12 | 2.31 |
| 21.88 | 4.06 | 2.69 |
| 22.17 | 4.01 | 3.93 |
| 22.85 | 3.89 | 19.52 |
| 23.55 | 3.78 | 17.00 |
| 23.82 | 3.74 | 8.29 |
| 24.57 | 3.62 | 6.95 |
| 24.86 | 3.58 | 6.20 |
| 25.13 | 3.54 | 3.53 |
| 25.66 | 3.47 | 14.62 |
| 26.60 | 3.35 | 9.45 |
| 26.86 | 3.32 | 4.40 |
| 27.73 | 3.22 | 3.98 |
| 28.10 | 3.18 | 5.25 |
| 29.17 | 3.06 | 3.06 |
| 29.52 | 3.03 | 2.80 |
| 30.01 | 2.98 | 0.88 |
| 30.71 | 2.91 | 2.77 |
| 30.94 | 2.89 | 2.76 |
| 31.71 | 2.82 | 1.45 |
| 32.76 | 2.73 | 0.78 |
| 33.33 | 2.69 | 3.58 |
| 33.84 | 2.65 | 1.93 |
| 34.30 | 2.61 | 2.54 |
| 34.86 | 2.57 | 1.71 |
| 35.73 | 2.51 | 0.52 |
| 38.00 | 2.37 | 2.14 |

Example 3 Preparation of Form CS2

13.44 mg of acetic acid complex obtained in example 2 was heated to 190° C. using DSC (heating rate was 20° C./min), then white solid was obtained and the yield was 100%.

Figure 4:
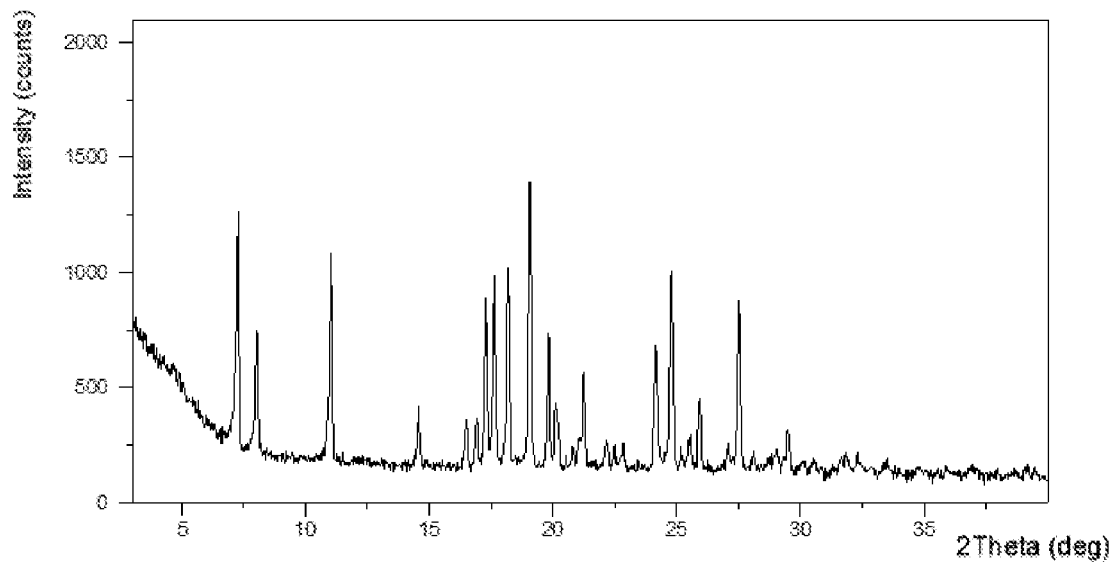
FIG. 4 shows an XRPD pattern of Form CS2.

The obtained crystalline solid was identified to be Form CS2 of the present disclosure, of which the XRPD pattern was shown in FIG. 4 and data were listed in Table 3.

TABLE 3

| 2θ (±0.2°) | d spacing | Intensity % |
|---|---|---|
| 7.21 | 12.27 | 93.05 |
| 7.96 | 11.11 | 44.90 |
| 10.96 | 8.07 | 100.00 |
| 14.49 | 6.11 | 23.84 |
| 16.41 | 5.40 | 17.71 |
| 16.85 | 5.26 | 18.87 |
| 17.22 | 5.15 | 52.97 |
| 17.55 | 5.05 | 75.03 |
| 18.10 | 4.90 | 63.73 |
| 18.99 | 4.67 | 99.04 |
| 19.74 | 4.50 | 44.06 |
| 20.02 | 4.44 | 23.83 |
| 21.16 | 4.20 | 33.08 |
| 22.10 | 4.02 | 11.72 |
| 22.74 | 3.91 | 6.59 |
| 24.07 | 3.70 | 40.39 |
| 24.70 | 3.61 | 62.60 |
| 25.45 | 3.50 | 10.82 |
| 25.84 | 3.45 | 24.65 |
| 27.43 | 3.25 | 54.09 |
| 29.42 | 3.04 | 11.84 |
| 31.72 | 2.82 | 6.40 |
| 33.32 | 2.69 | 3.60 |
| 36.89 | 2.44 | 2.41 |

Figure 5:
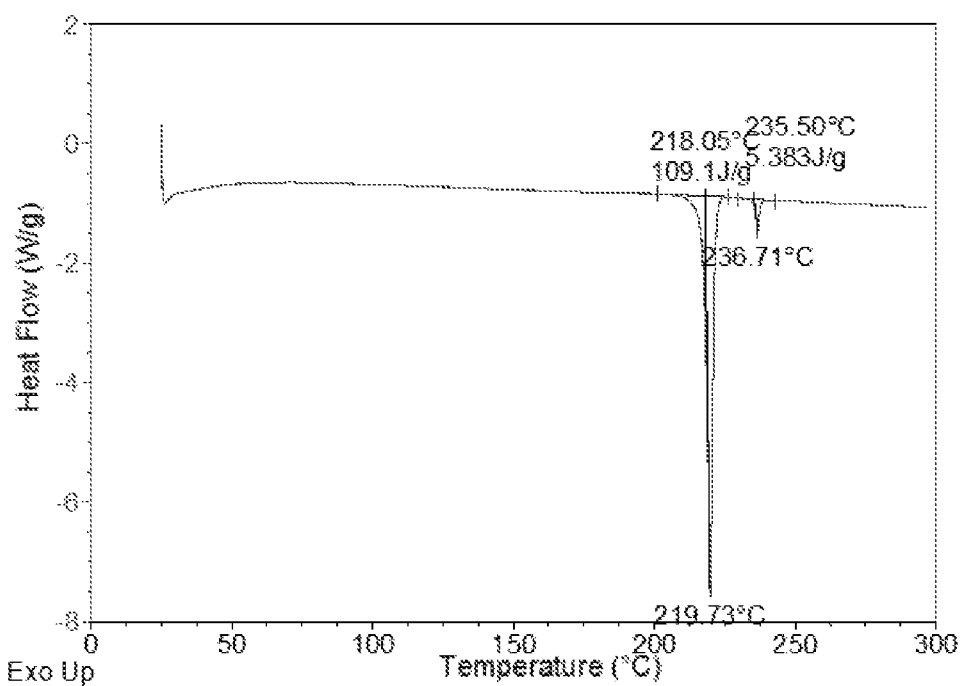
FIG. 5 shows a DSC curve of Form CS2.

The DSC curve of Form CS2 is substantially as depicted in FIG. 5, and one endothermic peak is at around 218° C.

Figure 6:
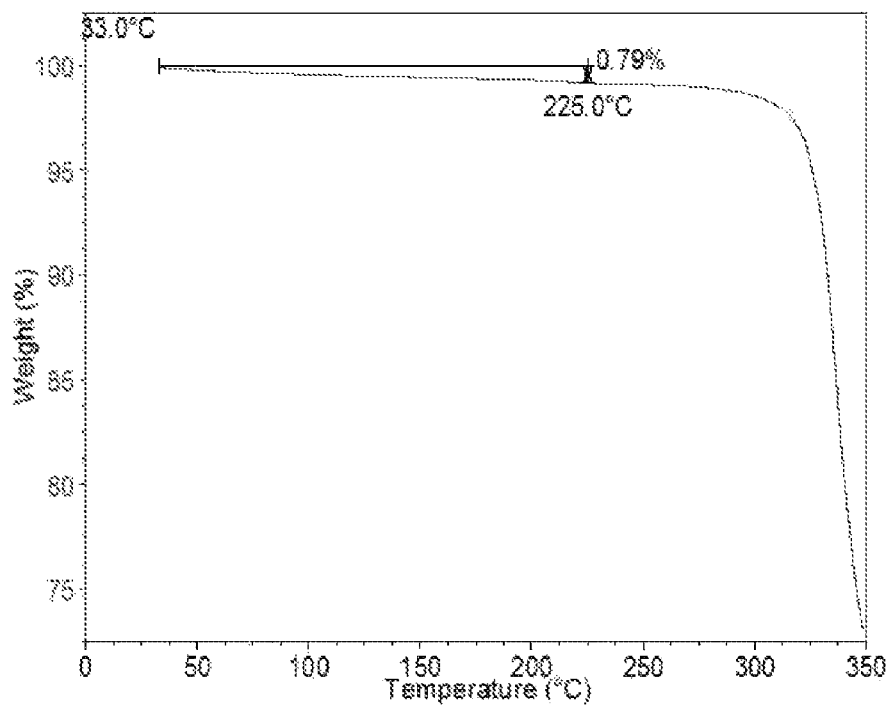
FIG. 6 shows a TGA curve of Form CS2.

The TGA curve of Form CS2 shows about 0.8% weight loss when heated to 225° C., which is substantially as depicted in FIG. 6.

Example 4 Preparation of Form CS2

11.99 mg of acetic acid complex obtained in example 2 was heated to 190° C. using DSC (heating rate was 20° C./min), then white solid was obtained and the yield was 100%.

The obtained crystalline solid was identified to be Form CS2 of the present disclosure, of which the XRPD data were listed in Table 4.

TABLE 4

| 2θ (±0.2°) | d spacing | Intensity % |
| --- | --- | --- |
| 4.66 | 18.95 | 3.42 |
| 7.20 | 12.27 | 77.66 |
| 7.96 | 11.10 | 42.37 |
| 10.96 | 8.07 | 73.49 |
| 14.48 | 6.12 | 19.49 |
| 16.42 | 5.40 | 15.30 |
| 16.84 | 5.27 | 17.15 |
| 17.22 | 5.15 | 53.82 |
| 17.55 | 5.05 | 66.01 |
| 18.11 | 4.90 | 68.63 |
| 18.99 | 4.67 | 100.00 |
| 19.74 | 4.50 | 45.19 |
| 20.03 | 4.43 | 22.38 |
| 21.16 | 4.20 | 34.08 |
| 22.09 | 4.02 | 9.57 |
| 22.75 | 3.91 | 7.19 |
| 24.08 | 3.70 | 43.90 |
| 24.70 | 3.60 | 68.98 |
| 25.43 | 3.50 | 10.22 |
| 25.84 | 3.45 | 25.34 |
| 26.98 | 3.31 | 8.31 |
| 27.43 | 3.25 | 58.41 |
| 28.01 | 3.19 | 5.37 |
| 29.40 | 3.04 | 13.88 |
| 31.70 | 2.82 | 4.55 |
| 36.88 | 2.44 | 2.93 |

Example 5 Preparation of Form CS2

11.02 mg of acetic acid complex obtained in example 2 was heated to 190° C. using DSC (heating rate was 20° C./min), then white solid was obtained and the yield was 100%.

The obtained crystalline solid was identified to be Form CS2 of the present disclosure, of which the XRPD data were listed in Table 5.

TABLE 5

| 2θ (±0.2°) | d spacing | Intensity % |
| --- | --- | --- |
| 7.20 | 12.28 | 76.37 |
| 7.96 | 11.11 | 45.46 |
| 10.96 | 8.07 | 81.95 |
| 14.49 | 6.11 | 23.88 |
| 16.40 | 5.41 | 20.81 |
| 16.83 | 5.27 | 16.35 |
| 17.21 | 5.15 | 48.61 |
| 17.54 | 5.06 | 64.96 |
| 18.09 | 4.90 | 65.77 |
| 18.98 | 4.68 | 100.00 |
| 19.73 | 4.50 | 44.51 |
| 20.02 | 4.44 | 21.98 |
| 21.16 | 4.20 | 40.14 |
| 22.73 | 3.91 | 8.18 |
| 24.08 | 3.70 | 38.80 |

TABLE 5-continued

| 2θ (±0.2°) | d spacing | Intensity % |
| --- | --- | --- |
| 24.70 | 3.60 | 68.19 |
| 25.82 | 3.45 | 24.73 |
| 27.44 | 3.25 | 49.23 |
| 29.42 | 3.04 | 9.45 |
| 31.84 | 2.81 | 4.07 |

Example 6 Hygroscopicity of Form CS2 and Pattern 4 of patent CN105960407A

The description of hygroscopicity and definition of hygroscopic weight gain (Chinese Pharmacopoeia 2015 edition general rule 9103 Drug hygroscopic test guidelines, test at 25° C.+/−1° C., 80% RH):

Deliquescent: sufficient water is absorbed to form a liquid;
Very hygroscopic: increase in mass is equal to or greater than 15 percent;
Hygroscopic: increase in mass is less than 15 percent and equal to or greater than 2 percent;
Slightly hygroscopic: increase in mass is less than 2 percent and equal to or greater than 0.2 percent.
Non or almost non-hygroscopic: increase in mass is less than 0.2%.

Those skilled in the art will understand that under the teachings of this specification some modifications or variations can be made to the present disclosure. Any equivalent and any equivalent variations or modifications according to the spirit of the present disclosure should be covered by the protective scope of the claims.

Figure 7:
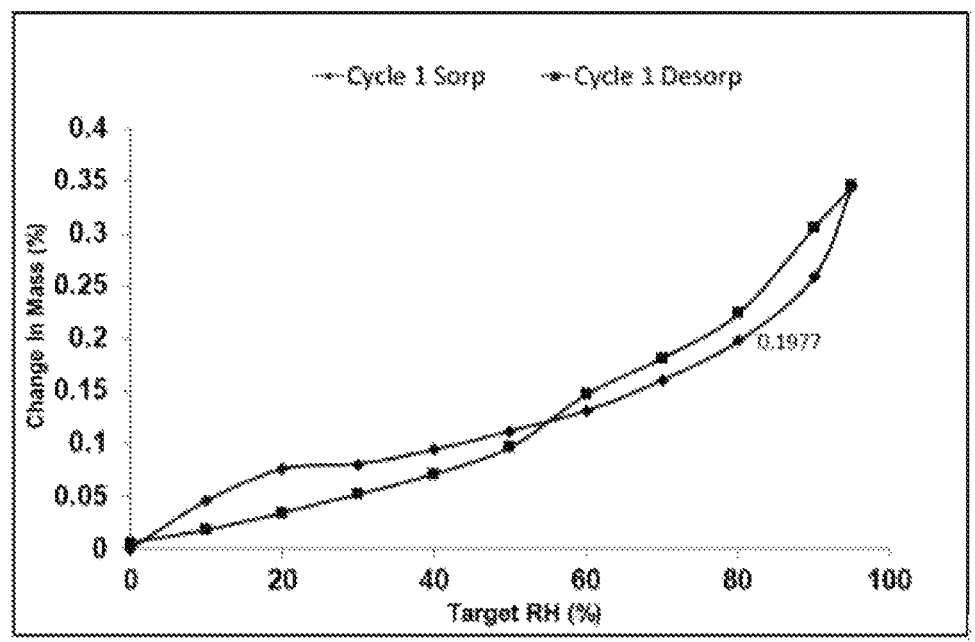
FIG. 7 shows a DVS plot of Form CS2.
Figure 8:
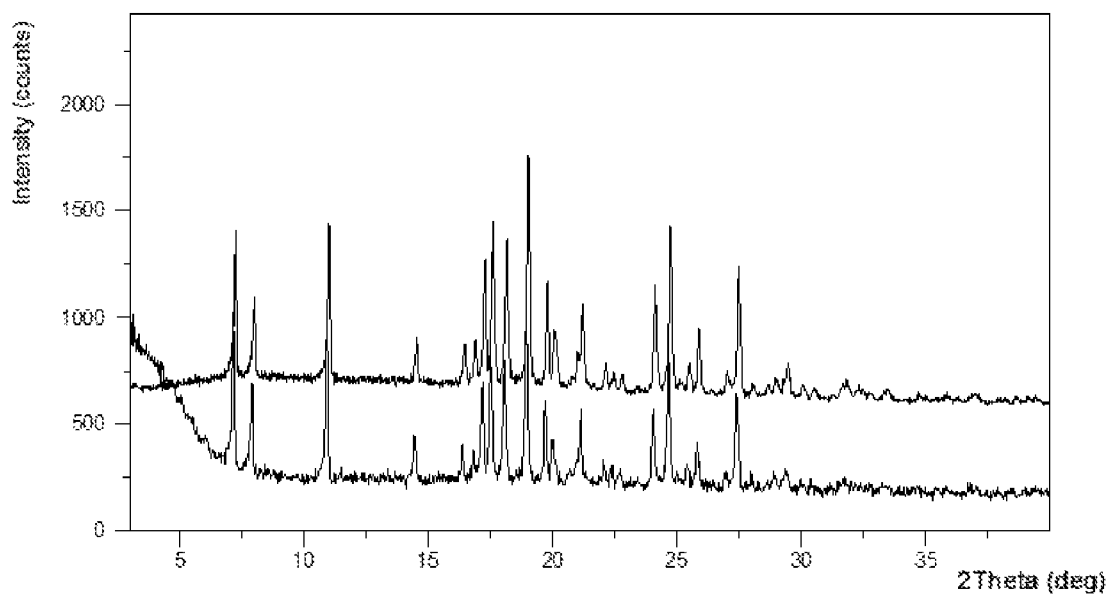
FIG. 8 shows an XRPD pattern overlay of Form CS2 before and after DVS (top: XRPD pattern after DVS; bottom: XRPD pattern before DVS).
Figure 17:
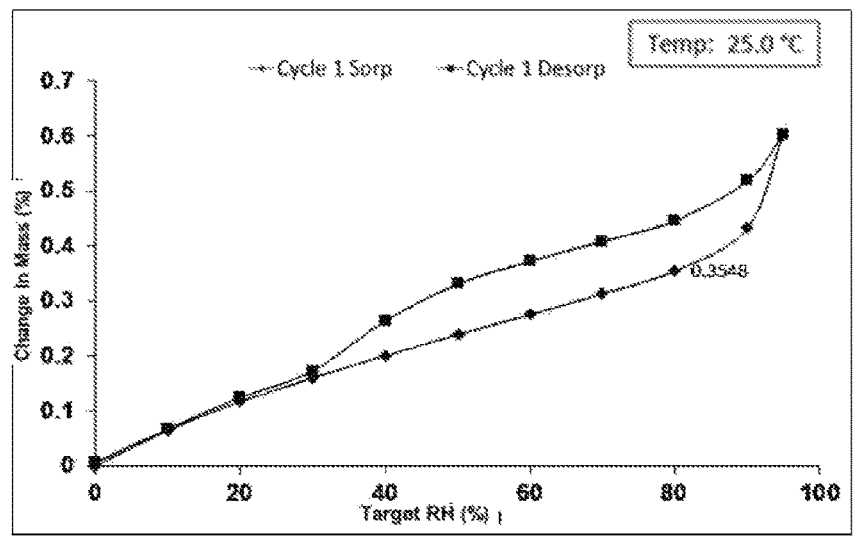
FIG. 17 shows a DVS plot of Pattern 4 of CN105960407A.

Dynamic vapor sorption (DVS) was applied to test hygroscopicity of Form CS2 and Pattern 4 in patent CN105960407A (hereinafter referred to as patent Pattern 4) on about 10 mg of samples. The weight gains at each relative humidity were recorded in a cycle of 0-95%-0 RH. The results were listed in Table 6. The DVS plot of Form CS2 was displayed in FIG. 7, and the XRPD overlay before and after DVS was displayed in FIG. 8, indicating no form change was observed for Form CS2. The DVS plot of Pattern 4 was displayed in FIG. 17.

TABLE 6

| Weight gain (%) | Relative Humidity Weight gain under 80% Relative Humidity |
| --- | --- |
| Form CS2 | 0.198% |
| Pattern 4 | 0.350% |

The results show that Form CS2 of the present disclosure is almost non-hygroscopic, and the hygroscopicity of Form CS2 is lower than that of patent Pattern 4 under 80% RH. Hygroscopicity of drugs is closely related to selection of appropriate packaging, storage conditions, formulation process and dosage form. Inappropriate packaging and storage condition will induce appearance changes of drugs with higher hygroscopicity, such as agglomeration, deliquescence and color-change, etc., and inner quality changes will be triggered consequently. Low hygroscopic drugs have low demands on packaging and storage condition, which is ideal for long-term storage. The cost of package, storage and quality control decreases. Meanwhile, no special drying condition is needed during preparation of crystal form with low hygroscopicity, which simplifies the preparation and downstream process of drugs, makes it easier for industrial production, and decreases the drug research and development costs remarkably.

Example 7 Stability Study of Form CS1 and Form CS2

Form CS1 of the present disclosure was stored under 25° C./60% RH and 40° C./75% RH for 3 weeks. Form CS2 of the present disclosure was stored under 25° C./60% RH, 40° C./75% RH and 60° C./75% RH for 3 weeks. XRPD was applied to test the crystalline form and the results were shown in Table 7 and Table 8. The XRPD overlays of Form CS1 and Form CS2 before and after storage in above conditions for 3 weeks were shown in FIG. 18 and FIG. 19.

TABLE 7

Figure 18:
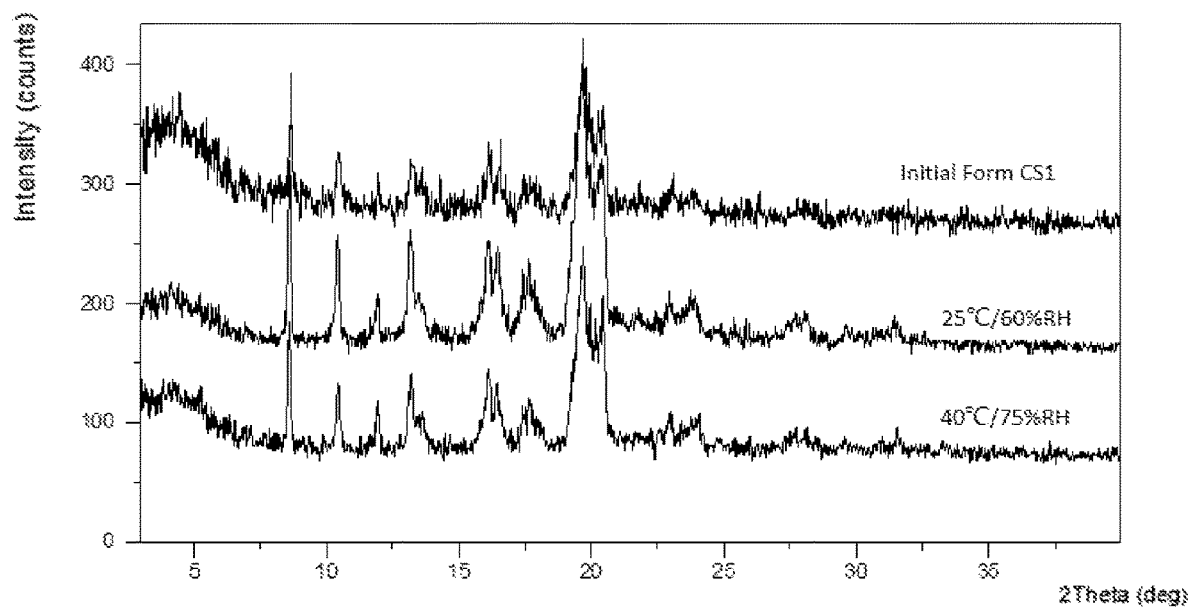
FIG. 18 shows an XRPD pattern overlay of Form CS1 before and after being placed under the conditions of 25° C./60% RH and 40° C./75% RH for three-week.

| Initial solid form | Condition | Time | Solid form change |
|---|---|---|---|
| Form CS1 | 25° C./ 60% RH | 3 weeks | No form change of Form CS1 (as shown in FIG. 18) |
|  | 40° C./ 75% RH | 3 weeks | No form change of Form CS1 (as shown in FIG. 18) |

TABLE 8

Figure 19:
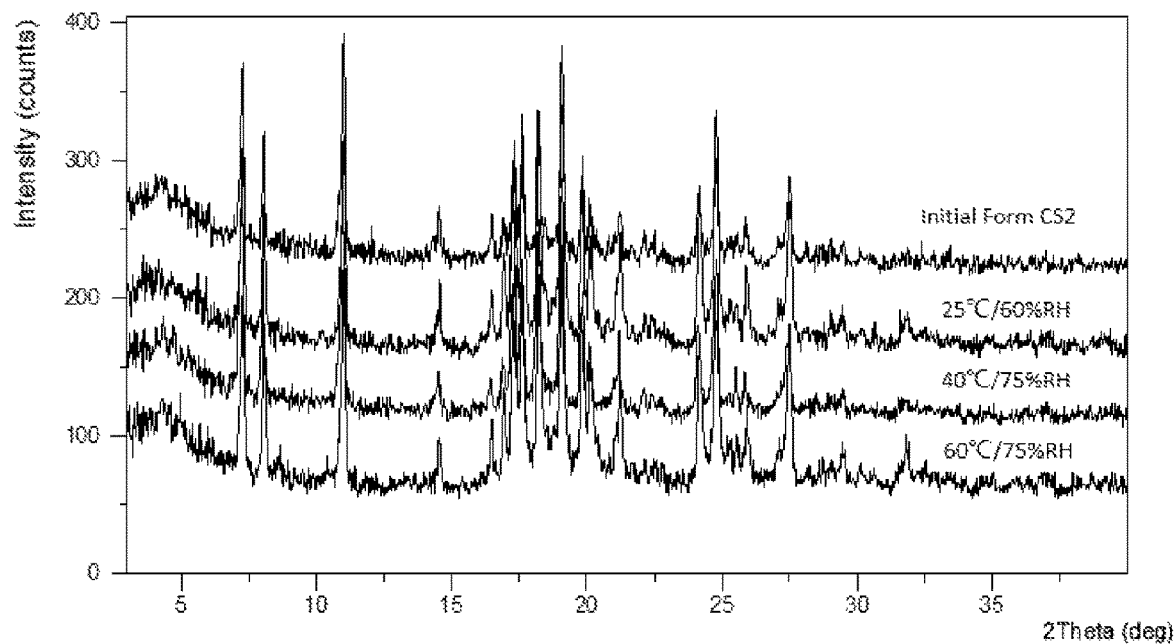
FIG. 19 shows an XRPD pattern overlay of Form CS2 before and after being placed under the conditions of 25° C./60% RH, 40° C./75% RH and 60° C./75% RH for three-week.

| Initial solid form | Condition | Time | Solid form change |
|---|---|---|---|
| Form CS2 | 25° C./ 60% RH | 3 weeks | No form change of Form CS2 (as shown in FIG. 19) |
|  | 40° C./ 75% RH | 3 weeks | No form change of Form CS2 (as shown in FIG. 19) |
|  | 60° C./ 75% RH | 3 weeks | No form change of Form CS2 (as shown in FIG. 19) |

The results show that Form CS1 doesn't change for at least 3 weeks when placed under the conditions of 25° C./60% RH and 40° C./75% RH. The crystalline form of Form CS2 doesn't change for at least 3 weeks when placed under the conditions of 25° C./60% RH, 40° C./75% RH and 60° C./75% RH. Form CS1 and Form CS2 of the present disclosure have good stabilities.

Example 8 Solubility Comparison Study of Form CS1, Form CS2 and Pattern 4 in Patent CN105960407A Saturated solutions of Form CS1, Form CS2 of the present disclosure and Pattern 4 in patent CN105960407A (hereinafter referred to as patent Pattern 4) were prepared in SGF (simulated gastric fluids), FeSSIF (fed state simulated intestinal fluids, pH=5.0), FaSSIF (fasted state simulated intestinal fluids, pH=6.5) and pure water. After equilibrated for 1 h, 4 h and 24 h, concentrations of the saturated solutions were measured by HPLC. The results were listed in Table 9-12.

TABLE 9

Solubility of each crystalline form in SGF

|  | Solubility | | |
|---|---|---|---|
| Solid form | 1 h (mg/mL) | 4 h (mg/mL) | 24 h (mg/mL) |
| Form CS1 | 3.23 | 3.30 | 0.82 |
| Form CS2 | 1.31 | 1.32 | 0.56 |
| Patent Pattern 4 | 1.02 | 1.07 | 0.46 |

TABLE 10

Solubility of crystalline forms in FaSSIF

|  | Solubility | | |
|---|---|---|---|
| Solid form | 1 h (mg/mL) | 4 h (mg/mL) | 24 h (mg/mL) |
| Form CS1 | 0.12 | 0.11 | 0.12 |
| Form CS2 | 0.05 | 0.05 | 0.04 |
| Patent Pattern 4 | 0.02 | 0.02 | 0.02 |

TABLE 11

Solubility of crystalline forms in FeSSIF

|  | Solubility | | |
|---|---|---|---|
| Solid form | 1 h (mg/mL) | 4 h (mg/mL) | 24 h (mg/mL) |
| Form CS1 | 0.20 | 0.20 | 0.25 |
| Form CS2 | 0.09 | 0.10 | 0.08 |
| Patent Pattern 4 | 0.03 | 0.03 | 0.03 |

TABLE 12

Solubility of crystalline forms in water

|  | Solubility | | |
|---|---|---|---|
| Solid form | 1 h (mg/mL) | 4 h (mg/mL) | 24 h (mg/mL) |
| Form CS1 | 0.12 | 0.09 | 0.21 |
| Form CS2 | 0.04 | 0.04 | 0.04 |
| Patent Pattern 4 | 0.02 | 0.01 | 0.01 |

The results show that the solubilities of Form CS1 and Form CS2 of the present disclosure are higher than that of patent Pattern 4 after equilibrated for 1 h, 4 h and 24 h in above saturated solutions. The improvement of solubility decreases the difficulty of formulation process development, since for crystal form with adequately high solubility, conventional formulation process development can be applied. While for crystal form with low solubility, more complex formulation process will be developed for ideal bioavailability. In addition, the higher solubilities of Form CS1 and Form CS2 reduce drug dose without affecting drug efficacy, thereby reducing the drug's side effects and improving drug safety.

Figure 20:
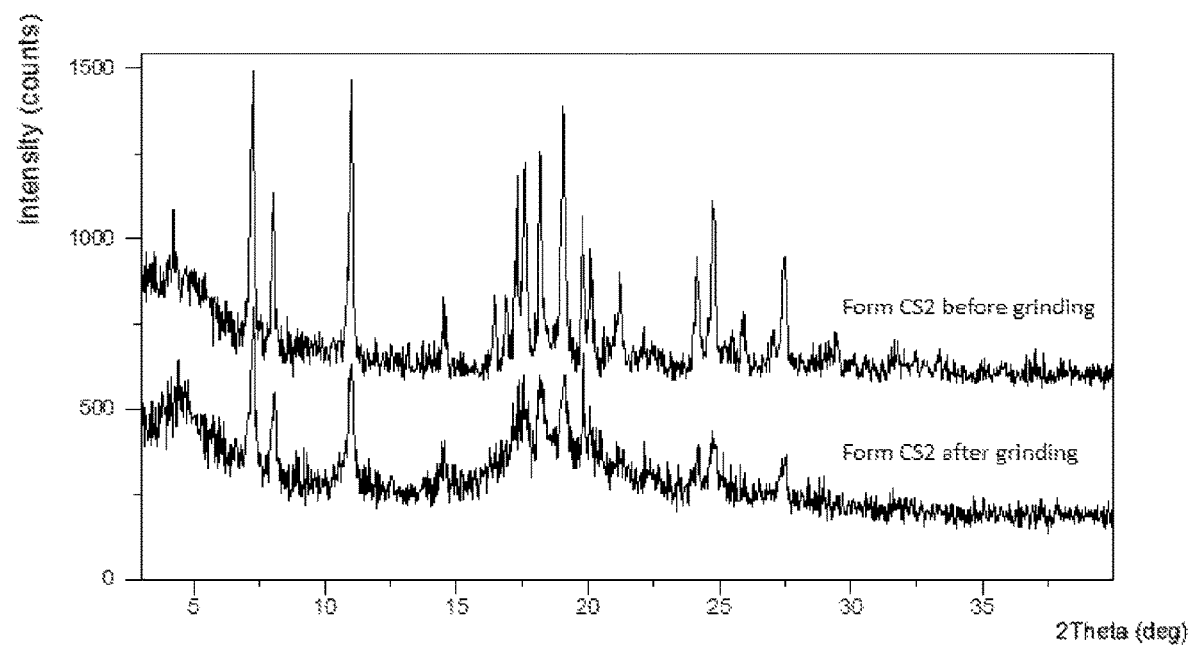
FIG. 20 shows an XRPD pattern overlay of Form CS2 before and after grinding.
Figure 21:
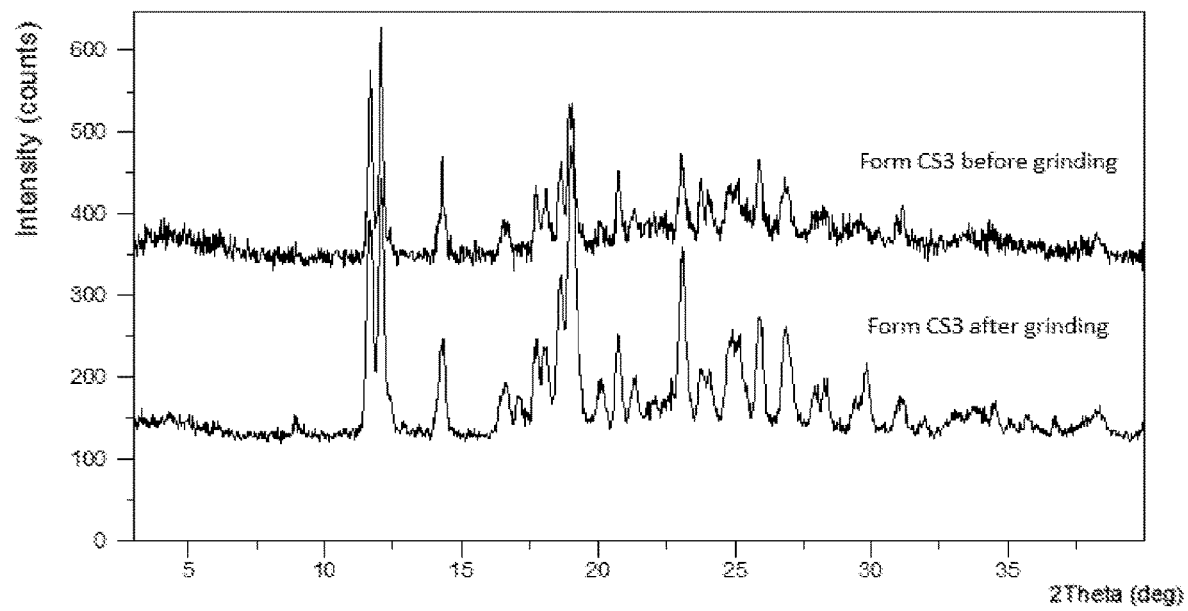
FIG. 21 shows an XRPD pattern overlay of Form CS3 before and after grinding.
Figure 22:
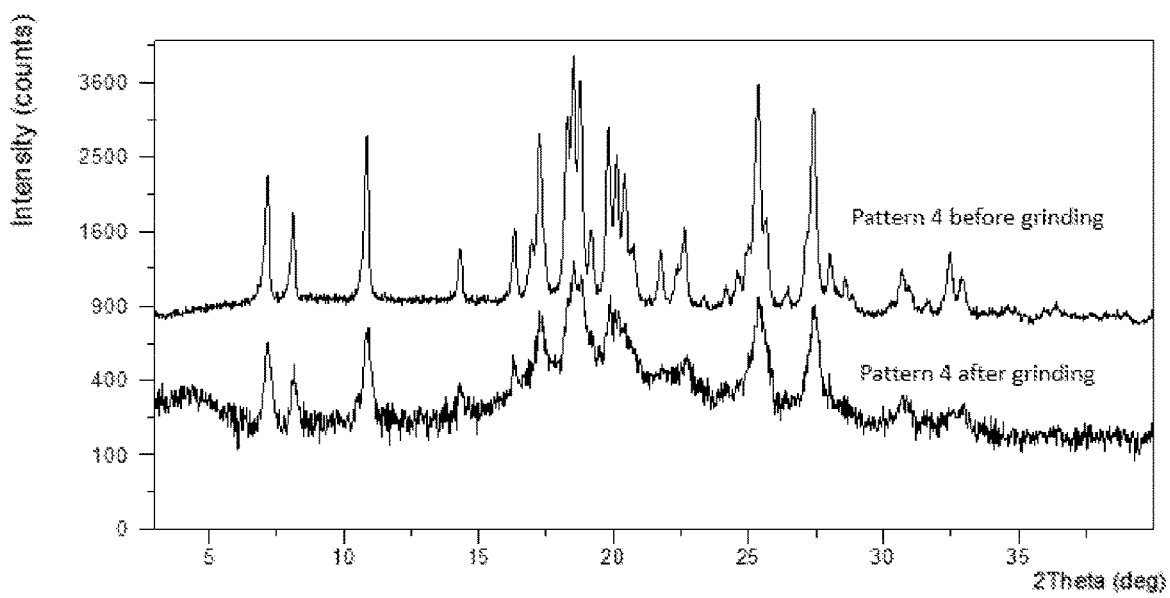
FIG. 22 shows an XRPD pattern overlay of Pattern 4 of CN105960407A before and after grinding.

Example 9 Mechanical Stability Study of Form CS2, Form CS3 and Pattern 4 in Patent CN105960407A XRPD was applied to test the crystalline forms of Form CS2, Form CS3 and Pattern 4 in patent CN105960407A before and after grinding. The test results were shown in FIG. 20, FIG. 21 and FIG. 22.

The results show that compared with Pattern 4 in patent CN105960407A, Form CS2 and Form CS3 have better mechanical stabilities. Better mechanical stability means maintaining stable physical and chemical properties under the action of certain mechanical forces. Crystalline drug with better mechanical stability is more stable in formulation process, and there is no need to worry about crystalline transformation caused by mechanical forces in the downstream formulation processes. Mechanically stable crystalline forms can significantly reduce the cost of production and improved drug quality, which has strong economic value.

The invention claimed is:

1. A crystalline form CS1 of Filgotinib, wherein the X-ray powder diffraction pattern shows characteristic peaks at 2theta values of 10.3°±0.2°, 13.7°±0.2° and 16.1°±0.2° using Cu-Kα radiation.

2. The crystalline form CS1 of Filgotinib according to claim 1, wherein the X-ray powder diffraction pattern shows one or more characteristic peaks at 2theta values of 18.0°±0.2°, 21.7°±0.2° and 24.7°±0.2° using Cu-Kα radiation.

3. The crystalline form CS1 of Filgotinib according to claim 1, wherein the X-ray powder diffraction pattern shows one or two characteristic peaks at 2theta values of 8.6°±0.2° and 19.4°±0.2° using Cu-Kα radiation.

4. A process for preparing crystalline form CS1 according to claim 1, wherein the process comprises: suspending Filgotinib hydrochloride into halogenated aromatic hydrocarbons with adding base, stirring for crystallization at certain temperature, then isolating and drying the solid to obtain a halogenated aromatic hydrocarbon solvate and Form CS1 is obtained via a desolvation process by heating the halogenated aromatic hydrocarbon solvate.

5. The process for preparing crystalline form CS1 according to claim 4, wherein said halogenated aromatic hydrocarbon is a solvent or a mixture of solvents selected from halogenated aromatic hydrocarbons; said base is inorganic base; said crystallization temperature is 25-0° C.; said desolvation temperature is 150-195° C.

6. A crystalline form CS2 of Filgotinib, wherein the X-ray powder diffraction pattern shows characteristic peaks at 2theta values of 17.5°±0.2°, 18.1°±0.2° and 8.0°±0.2° using Cu-Kα radiation.

7. The crystalline form CS2 of Filgotinib according to claim 6, wherein the X-ray powder diffraction pattern shows 1 or more characteristic peaks at 2theta values of 24.7°±0.2°, 17.2°±0.2° and 27.4°±0.2°.

8. The crystalline form CS2 of Filgotinib according to claim 6, wherein the X-ray powder diffraction pattern shows 1 or more characteristic peaks at 2theta values of 7.2°±0.2°, 11.0°±0.2° and 19.0°±0.2°.

9. A process for preparing crystalline form CS2 according to claim 6, wherein the process comprises: suspending Filgotinib hydrochloride into carboxylic acid with adding base, stirring for crystallization at certain temperature, isolating and drying the solid to obtain a carboxylic acid solvate and crystalline form CS2 is obtained via a desolvation process by heating the carboxylic acid solvate.

10. The process for preparing crystalline form CS2 according to claim 9, wherein said carboxylic acid is a carboxylic acid or a mixture carboxylic acid selected from $C_1$-$C_3$carboxylic acids; said base is inorganic base; said crystallization temperature is 25-0° C.; said desolvation temperature is 150-195° C.

11. A crystalline form CS3 of Filgotinib, wherein the X-ray powder diffraction pattern shows characteristic peaks at 2theta values of 11.8°±0.2°, 14.1°±0.2° and 17.8°±0.2° using Cu-Kα radiation.

12. The crystalline form CS3 of Filgotinib according to claim 11, wherein the X-ray powder diffraction pattern shows 1 or more characteristic peaks at 2theta values of 18.4°±0.2°, 20.5°±0.2° and 22.9°±0.2°.

13. The crystalline form CS3 of Filgotinib according to claim 11, wherein the X-ray powder diffraction pattern shows 1 or more characteristic peaks at 2theta values of 25.7°±0.2°, 11.5°±0.2° and 23.6°±0.2°.

14. A process for preparing crystalline form CS3 according to claim 11, wherein the process comprises: suspending Filgotinib hydrochloride into acetic acid with adding base, stirring for crystallization at certain temperature, isolating and drying to obtain Form CS3.

15. The process for preparing crystalline form CS3 according to claim 14, wherein said base is inorganic base; said crystallization temperature is 25-0° C.

16. A pharmaceutical composition, wherein said pharmaceutical composition comprises a therapeutically effective amount of crystalline form CS1 according to claim 1, and pharmaceutically acceptable carriers or excipients.

17. A method of treating rheumatoid arthritis or Crohn's disease, comprising administering to a patient in need thereof a therapeutically effective amount of the crystalline form CS1 according to claim 1.

18. A pharmaceutical composition, wherein said pharmaceutical composition comprises a therapeutically effective amount of crystalline form CS2 according to claim 6, and pharmaceutically acceptable carriers or excipients.

19. A pharmaceutical composition, wherein said pharmaceutical composition comprises a therapeutically effective amount of crystalline form CS3 according to claim 11, and pharmaceutically acceptable carriers or excipients.

20. A method of treating rheumatoid arthritis or Crohn's disease, comprising administering to a patient in need thereof a therapeutically effective amount of the crystalline form CS2 according to claim 6.

21. A method of treating rheumatoid arthritis or Crohn's disease, comprising administering to a patient in need thereof a therapeutically effective amount of the crystalline form CS3 according to claim 11.

* * * * *